United States Patent
Scholan et al.

(10) Patent No.: US 10,426,558 B2
(45) Date of Patent: Oct. 1, 2019

(54) PORT CONTROL

(71) Applicant: CMR Surgical Limited, Cambridge (GB)

(72) Inventors: Andrew Murray Scholan, Newmarket (GB); Ben Robert Chaplin, Cambridge (GB); Keith Marshall, Cambridge (GB); Luke David Ronald Hares, Cambridge (GB); Nikki Priyam Su-Ling Phoolchund, Cambridge (GB); Thomas Bates Jackson, Cambridge (GB)

(73) Assignee: Cambridge Medical Robotics Limited, Cambridge (GB)

(*) Notice: Subject to any disclaimer, the term of this patent is extended or adjusted under 35 U.S.C. 154(b) by 201 days.

(21) Appl. No.: 15/355,850

(22) Filed: Nov. 18, 2016

(65) Prior Publication Data
US 2017/0143435 A1    May 25, 2017

(30) Foreign Application Priority Data
Nov. 24, 2015    (GB) .................................. 1520754.1

(51) Int. Cl.
*G06F 19/00* (2018.01)
*A61B 34/30* (2016.01)
(Continued)

(52) U.S. Cl.
CPC .......... *A61B 34/30* (2016.02); *A61B 17/3421* (2013.01); *B25J 9/1615* (2013.01);
(Continued)

(58) Field of Classification Search
CPC ............ A61B 17/3421; A61B 17/3423; A61B 2017/3409; A61B 2034/302;
(Continued)

(56) References Cited

U.S. PATENT DOCUMENTS 9,480,534 B2 * 11/2016 Bowling .................. B25J 13/00
9,532,849 B2 *  1/2017 Anderson .............. A61B 90/57
(Continued)

FOREIGN PATENT DOCUMENTS

WO    WO 2014/190185 A1    11/2014

OTHER PUBLICATIONS

Search Report for corresponding UK Appl No. GB1520754.1, dated Apr. 19, 2016.

*Primary Examiner* — Harry Y Oh
(74) *Attorney, Agent, or Firm* — Renner, Otto, Boisselle & Sklar, LLP

(57) ABSTRACT

A locator of a surgical port of a surgical robot system, the surgical robot system comprising an instrument attached to a robot arm, the instrument having an instrument shaft able to pass through the surgical port to a surgical site, the locator comprising: an interface configured to couple to the surgical port; a mechanism configured to permit relative linear and/or rotational motion of the interface and the instrument shaft; and a controller comprising a processor operable to estimate the position of a part of the robot arm, the controller configured to control the mechanism in dependence on the estimated position of the part of the robot arm such that as the robot arm retracts the instrument from the patient, the locator moves the port away from the robot arm and provides a reaction force to keep the port in place.

20 Claims, 7 Drawing Sheets

(51) Int. Cl.
 *B25J 9/16* (2006.01)
 *B25J 15/00* (2006.01)
 *A61B 17/34* (2006.01)
 *A61B 90/00* (2016.01)

(52) U.S. Cl.
 CPC ....... *B25J 15/0019* (2013.01); *A61B 17/3423* (2013.01); *A61B 2017/3409* (2013.01); *A61B 2034/302* (2016.02); *A61B 2090/061* (2016.02); *Y10S 901/41* (2013.01)

(58) Field of Classification Search
 CPC ............... A61B 2090/061; A61B 34/30; B25J 15/0019; B25J 9/1615; Y10S 901/41
 See application file for complete search history.

(56) References Cited

U.S. PATENT DOCUMENTS

| | | | |
|---|---|---|---|
| 9,820,818 B2* | 11/2017 | Malackowski | A61B 34/32 |
| 2011/0264136 A1* | 10/2011 | Choi | A61B 34/71 |
| | | | 606/205 |
| 2013/0211423 A1* | 8/2013 | Blumenkranz | A61B 17/3462 |
| | | | 606/130 |
| 2013/0345718 A1* | 12/2013 | Crawford | A61B 17/025 |
| | | | 606/130 |
| 2014/0180308 A1 | 6/2014 | von Grunberg | |
| 2014/0236177 A1* | 8/2014 | Verner | A61B 17/3462 |
| | | | 606/130 |
| 2015/0366620 A1* | 12/2015 | Cameron | A61B 17/3421 |
| | | | 606/130 |
| 2016/0001448 A1* | 1/2016 | Rothfuss | A61B 34/30 |
| | | | 294/192 |
| 2017/0049522 A1* | 2/2017 | Kapadia | A61B 34/30 |

* cited by examiner

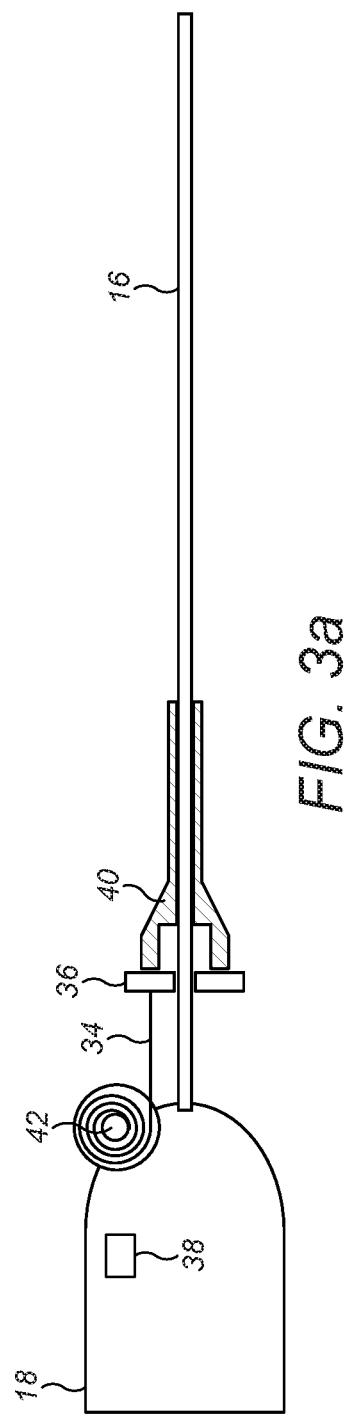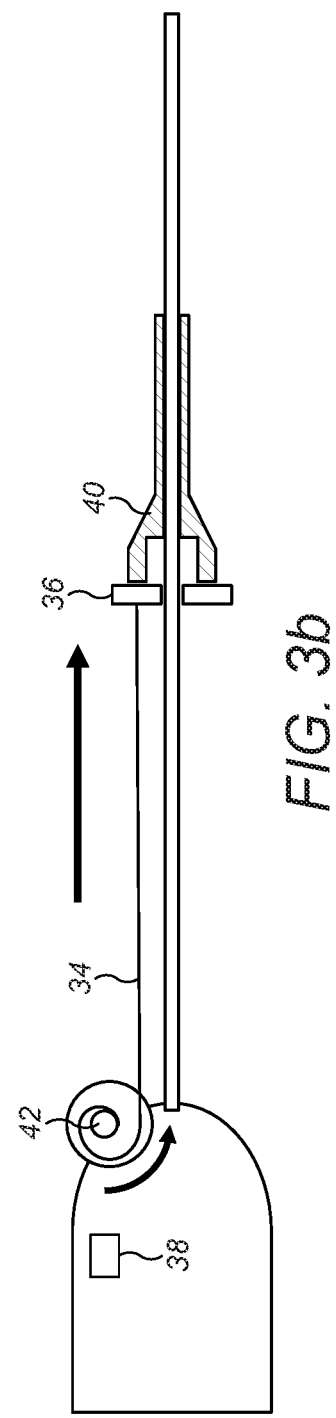

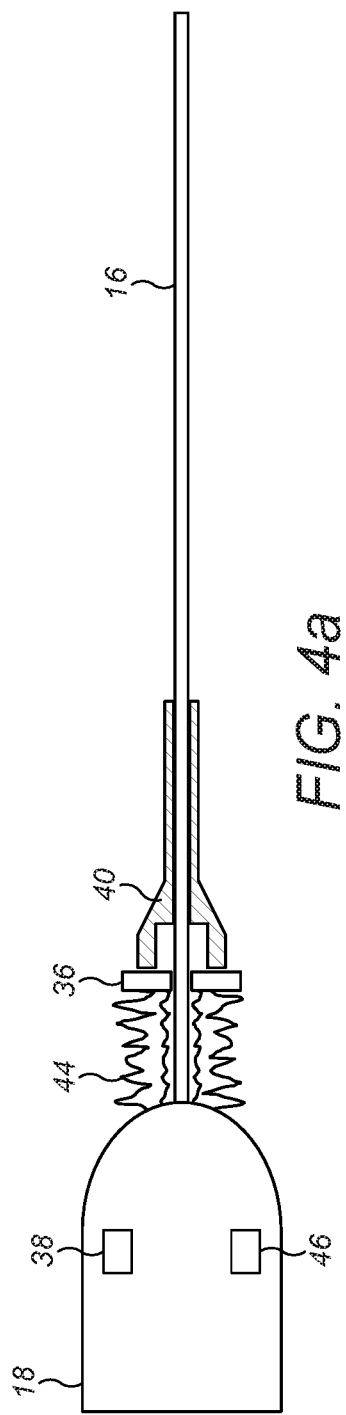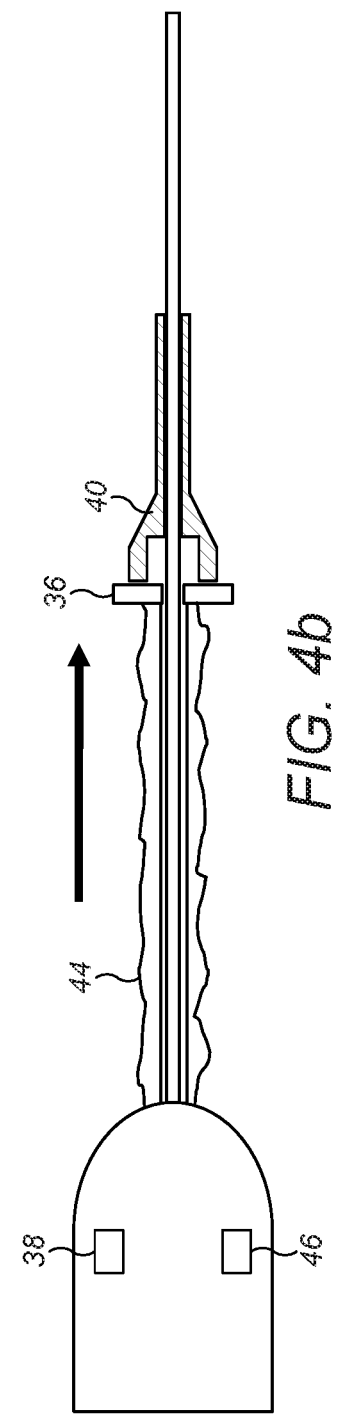

PORT CONTROL

CROSS-REFERENCE TO RELATED APPLICATIONS

This application claims benefit under 35 USC 119 of United Kingdom Application No. 1520754.1, filed Nov. 24, 2015. The contents of this application is hereby incorporated by reference in its entirety.

This invention relates to the positioning of surgical ports.

BACKGROUND

FIG. 1 illustrates part of an apparatus used for conventional robotic surgery. The apparatus comprises a robot arm 1, only the distal end of which is shown in FIG. 1. A rail 2 extends from the distal end of the arm towards a patient, whose skin is indicated at 3. At the end of the rail is a surgical instrument 4 which passes into the patient for performing surgery. The instrument enters the patient through an incision in the skin. To keep the incision clear, and to avoid the patient's skin being torn when the instrument is moved, a port 5 is located in the incision. The port is carried by the rail 2. The port is free to slide along the length of the rail as indicated by arrow 6, and the port clips into the incision. Because the port adheres to the tissue around the incision, when the robot arm 1 moves the instrument into and out of the patient during surgery a force is applied to the port. This force moves the port along the rail so that the port can stay in place in the incision.

This approach has a number of problems. First, the port needs some mechanism to bind to the incision in order that it will stay in place when the instrument is moved. This mechanism can enlarge the incision or cause damage to the tissue around the incision. Second, if the port is not properly secure in the incision it can be ripped out of the incision when the robot moves the instrument. This can again damage the incision. Finally, the mechanism relies on forces being applied to the port by the tissue around the incision. These forces can themselves cause damage to the tissue at the incision.

Similar problems arise in non-robotic laparoscopic surgery. However, in manual surgery the surgeon is standing next to the patient and can normally see or feel the signs of a port becoming loose or of excessive force being applied to the port. In robotic surgery the force feedback that a surgeon gets from a robot may be comparatively weak or imprecise, and with many other displays to look at the surgeon might not keep the ports under constant observation.

There is a need for an improved way of locating surgical ports.

SUMMARY OF THE INVENTION

According to one aspect of the invention there is provided a locator of a surgical port of a surgical robot system, the surgical robot system comprising an instrument attached to a robot arm, the instrument having an instrument shaft able to pass through the surgical port to a surgical site, the locator comprising: an interface configured to couple to the surgical port; a mechanism configured to permit relative linear and/or rotational motion of the interface and the instrument shaft; and a controller comprising a processor operable to estimate the position of a part of the robot arm, the controller configured to control the mechanism in dependence on the estimated position of the part of the robot arm such that as the robot arm retracts the instrument from the patient, the locator moves the port away from the robot arm and provides a reaction force to keep the port in place.

There may be provided a locator for a surgical port, the locator comprising: an interface for attachment to a portion of the surgical port; a mechanism for permitting linear relative motion of the interface and a robot arm; and a controller for controlling the position of the interface relative to the robot arm in dependence on the position of the robot arm; in which the mechanism is an engaging mechanism for engaging with an instrument shaft of an instrument coupled to the robot arm; or in which the locator comprises a seat for attachment to the robot arm and the mechanism links the seat and the interface, the mechanism comprising one of a single member allowing motion over the full extent of the linear relative motion and an articulated mechanism.

Suitably the mechanism permits linear relative motion of the seat and the interface.

There may be provided a locator for a surgical port, the locator comprising: an interface for coupling to the surgical port; an engaging mechanism for engaging with an instrument shaft of a robot arm to permit linear relative motion of the interface and the robot arm; and a controller for controlling the position of the interface relative to the robot arm in dependence on the position of the robot arm.

The interface may be coupled to a port body of the surgical port. Suitably the interface is attached to the port body. Suitably the interface is attached to the surgical port.

Suitably the controller is for controlling the position of the interface relative to the robot arm such that it is separately controlled from the control of the robot arm. Suitably the controller is for controlling the position of the interface relative to the robot arm such that it is separately controlled from the position of the robot arm. In other words, the interface can be controlled separately from the robot arm. The interface may move at the same time as the robot arm, but it need not do so.

Suitably the engaging mechanism is arranged to frictionally engage with the instrument shaft (or tool shaft). Suitably the engaging mechanism comprises frictional engagement means for frictionally engaging with the instrument shaft (or tool shaft). The frictional engagement means may comprise a roller. Suitably the frictional engagement means comprises more than one roller, such as opposing rollers for engaging with opposing sides of the instrument shaft. The engaging mechanism may comprise one or more rollers for frictionally engaging with opposing sides of the shaft. This can increase the stability of movement of the surgical port along the instrument shaft. The engaging mechanism may comprise a resilient portion for resiliently engaging with the shaft, for example to assist the frictional engagement between the engaging mechanism and the shaft. Suitably the frictional engagement means is resilient. At least one roller may be resilient.

The engaging mechanism may comprise gears. Suitably the gears are for permitting engagement of the engaging mechanism with the instrument shaft. Suitably the gears permit control of the relative position of the engaging mechanism and the instrument shaft. The instrument shaft may be provided with spaced ridges for coupling with the gears so as to permit the engaging mechanism to be driven relative to the shaft. In this way the coupling between the gears and the ridges can act as a rack and pinion. This arrangement can provide increased control over the relative movement between the interface and the robot arm (e.g. between the interface and the instrument shaft). For example this might reduce or prevent slipping of the engagement mechanism relative to the instrument shaft.

Suitably the locator comprises a driver for altering the configuration of the engaging mechanism. Suitably the driver is arranged for driving the frictional engagement means. Suitably the driver is arranged for driving the gears.

Suitably the locator is arranged to determine the relative movement between the interface and the instrument shaft and/or the location of the interface on the instrument shaft relative to a known location of the interface relative to the instrument shaft. The known location may be at the distal end of the instrument shaft. The known location may be at the proximal end of the instrument shaft.

Suitably the locator is arranged to sense the distance between the interface and a portion of the robot arm. Suitably the locator comprises a distance sensing means for sensing the distance between the interface and a portion of the robot arm. This can allow the locator to determine the location of the surgical port along the instrument, for example the distance of the surgical port from the proximal end of the instrument shaft. The distance sensing means may be a sensor. Suitably the distance sensing means is arranged to sense the distance wirelessly. The sensor may be a light sensor. Suitably the sensor is a laser sensor.

The locator may comprise a locator body. The distance sensing means, for example the sensor, may be provided in a position spaced from the locator body, for example on a portion of the robot arm. Suitably the distance sensing means is provided on the locator body.

The locator may comprise a connection for receiving power from an external source. Suitably the locator comprises a power source, such as a battery. The locator may comprise a wired connection to enable communication with a remote device. Suitably the locator comprises a wireless communication module for enabling wireless communication with a remote device. The remote device may be a portion of a robotic surgical system, for example a module thereof. Suitably the wireless communication module is arranged to communicate with the remote device using at least one of radio frequency radiation and infra-red radiation. Other types of wireless communication would also be possible. The locator body may comprise the wired connection and/or the wireless communication module.

Suitably the locator body comprises the controller. In this way, the locator can act autonomously to move the surgical port in response to movements of the robot arm.

There may be provided a locator for a surgical port, the locator comprising: a seat for attachment to a robot arm; an interface for coupling to the surgical port; a mechanism linking the seat and the interface, the mechanism permitting linear relative motion of the seat and the interface; and a controller for controlling the position of the seat relative to the interface in dependence on the position of the robot arm; wherein the mechanism comprises one of a single member permitting the linear relative motion and an articulated mechanism.

There may be provided a locator for a surgical port, the locator comprising: a seat for attachment to a robot arm; an interface for coupling to the surgical port; a mechanism linking the seat and the interface, the mechanism permitting linear relative motion of the seat and the interface, the mechanism comprising a single member permitting the linear relative motion; and a controller for controlling the position of the seat relative to the interface in dependence on the position of the robot arm.

Suitably the interface is attached to the surgical port.

Suitably the controller is for controlling the position of the seat relative to the interface such that it is separately controlled from the control of the robot arm. Suitably the controller is for controlling the position of the seat relative to the interface such that it is separately controlled from the position of the robot arm.

Suitably the single member is an extensible member for extending so as to permit the linear relative motion. Suitably the extensible member may be made of an extensible material, such as an expandable material. The extensible member may have a concertina-type form. Suitably the extensible member is an inflatable member, such as an inflatable sheath. Suitably the inflatable sheath is arranged to enclose at least a portion of the instrument or tool coupled to the robot arm. The inflatable member may be an inflatable bag for enclosing at least a portion of the instrument coupled to the robot arm. The extensible member may be part of a sterile drape, such as a sterile drape that covers at least a portion of a robotic surgical system for providing a sterile barrier between the robotic surgical system and a surgical site. The sterile drape may cover at least a portion of the robot arm.

Suitably the extensible member comprises an inlet port. The inlet port can be for allowing fluid such as gas into an interior of the extensible member. The extensible member may be arranged to extend in response to the inlet of fluid into the interior. The inlet port may be connectable to a fluid port on the robot arm. In this way, the extensible member can receive fluid through the robot arm so as to enable the extension of the extensible member. The extensible member may comprise an outlet port. The outlet port can be for allowing fluid such as gas to escape from the interior of the extensible member. This can facilitate the deflation or shrinking of the extensible member. The inlet port of the extensible member may provide an outlet fluid path from the inside of the extensible member. This outlet fluid path may additionally or alternatively provide for fluid to escape from the interior of the extensible member.

The inlet port of the extensible member may comprise, or be associated with, a pump for pumping fluid through the port. This can allow fluid to be pumped into and/or out of the extensible member, for example to inflate (expand) and/or deflate (contract) the extensible member. This can provide control over the amount by which the extensible member extends, and so the position of the seat relative to the interface.

The extensible member may be resilient. The extensible member may be made from a resilient material. This can provide a resistance to the extension of the extensible member, which can enable a more positive determination of its extension. It can also facilitate deflation or contraction of the extensible member by assisting in the outflow of fluid from its interior.

The source of fluid for extending the extensible member may be the same as the source of fluid for insufflating a surgical site.

The extensible member may be arranged to extend by at least one of unfurling and uncoiling. The extensible member may be a coiled member, such as a spiral tape, for example a metal tape.

The locator may comprise an extensible member housing for housing the extensible member, for example when it is in a non-extended state, and/or when it is at least partially retracted. For example, the housing may house the coiled member, such as the coil of tape. Suitably the housing is provided on a portion of the robot arm. This can minimise the size and/or weight of the surgical port and its attachments.

The locator may comprise a driver for altering the configuration of the extensible member. The driver may comprise the pump.

There may be provided a locator for a surgical port, the locator comprising: a seat for attachment to a robot arm; an interface for coupling to the surgical port; a mechanism linking the seat and the interface, the mechanism being articulated and permitting linear relative motion of the seat and the interface; and a controller for controlling the position of the seat relative to the interface in dependence on the position of the robot arm.

The robot arm may have a series of articulations along its length for permitting movement of the distal end of the robot arm relative to the proximal end of the robot arm. The seat may be attached to the robot arm proximally of (i.e. further from the distal end of the arm than) the most distal articulation of the arm.

The most distal articulation of the arm may permit rotation about an axis substantially parallel to an axis along which the mechanism permits the linear relative motion, such as the linear relative motion of the seat and the interface.

Suitably the articulated mechanism comprises a plurality of joints between the seat and the interface. Each of the joints may be a revolute joint or a prismatic joint. Any combination of revolute joints and prismatic joints may be used. Other joint types are also possible, in any combination.

The locator may comprise a driver for applying a force between the seat and the interface to alter the configuration of the mechanism. The controller may comprise the driver. The driver may comprise a motor, for example an electric motor. The driver may comprise a hydraulically or pneumatically operable piston.

The mechanism may permit solely linear relative motion of the seat and the interface or of the robot arm and the interface.

There may be provided a locator for a surgical port, the locator comprising: a base for attachment to a portion of a patient support; an interface for coupling to the surgical port; a support mechanism linking the base and the interface, the support mechanism permitting at least one of translational and rotational movement of the interface relative to the base; and a controller for controlling at least one of the position and orientation of the interface relative to the base in dependence on the position of the robot arm.

Suitably the interface is attached to the surgical port. Suitably the controller is for controlling at least one of the position and orientation of the interface relative to the base such that it is separately controlled from the control of the robot arm. Suitably the controller is for controlling at least one of the position and orientation of the interface relative to the base such that it is separately controlled from the position of the robot arm.

Suitably, where the support mechanism permits one of the translational and rotational movement of the interface relative to the base, the controller is arranged to control a respective one of the position and orientation of the interface relative to the base. Suitably the support mechanism permits both translational and rotational movement of the interface relative to the base and the controller is for controlling both the position and orientation of the interface relative to the base in dependence on the position of the robot arm.

In other words, the support mechanism can allow the interface, and also for example a surgical port coupled to the interface, to be moved to a desired location or position. The support mechanism may provide stable support at this location. In other words, once the interface has been positioned as desired, the support mechanism may restrict undesired further movement from this position. The support mechanism may be arranged to permit further desired movement. Suitably the support mechanism comprises a lock. The lock may have a locked and an unlocked configuration. Suitably in the unlocked configuration the lock will permit movement of the support mechanism. The movement permitted by the unlocked configuration may include at least one of translational and rotational movement. Suitably the support mechanism permits translational movement of the interface relative to the base when the lock is in the unlocked configuration.

Suitably in the locked configuration the lock will restrict or prevent movement of the support mechanism. The movement restricted by the locked configuration may include at least one of the translational and rotational movement. Suitably the support mechanism restricts translational movement of the interface relative to the base when the lock is in the locked configuration.

The support mechanism may comprise a support arm for permitting movement of the interface relative to the base. Suitably the support arm is an articulated support arm. Suitably the support arm comprises at least one joint. The lock may be arranged to permit and/or restrict movement of the at least one joint or articulation of the support arm.

The support mechanism may comprise a belt such as a solid belt for linking the base and the interface. This can provide structural rigidity. The structural rigidity may be provided by the rigidity of the support mechanism itself, or by the holding of an object by the support mechanism. That is to say, a non-rigid belt can provide structural rigidity by, for example, being held against an object such as a patient. The support mechanism can be held against the object by tension.

The support mechanism may comprise a rotational mechanism permitting rotation of the interface relative to the base. The rotational mechanism may comprise a gimbal system.

The support mechanism may comprise a driver for driving the support mechanism. Driving the support mechanism can include altering the configuration of the support mechanism. Suitably the driver is arranged to alter the translational configuration of the interface relative to the base. Suitably the driver is arranged to alter the rotational configuration of the interface relative to the base. The gimbal system may comprise the driver. The gimbal system may be driven by the driver to control the orientation of the gimbal system. In this way the orientation of the surgical port can be controlled.

The locator may have a surgical port attached to the interface.

There may be provided a surgical robot having: a robot arm, and a locator as defined in any aspect above coupled to the robot arm. The locator may be attached to the robot arm.

The surgical robot may comprise a surgical tool or instrument attached to the robot arm. A portion of the surgical tool may be arranged to pass through the surgical port. The surgical tool may be substantially unsupported by the locator.

There may be provided a surgical robot having: a robot arm, a surgical tool or instrument attached to the robot arm, and a locator as defined in any aspect above coupled to the instrument. The locator may be attached to the instrument.

The controller may comprise a processor operable to estimate the position of a part of the arm and to set the position of the seat relative to the interface in dependence on the estimated position. The controller may comprise a processor operable to estimate the position of a part of the arm and to set the position of the interface relative to a portion of the arm in dependence on the estimated position. The controller may comprise a processor operable to estimate the position of a part of the arm and to set the position and/or orientation of the interface relative to the base in dependence on the estimated position.

The surgical port may comprise an inlet port. Suitably the inlet port provides a fluid path into a port body of the surgical port. The port body may comprise a chamber. Suitably the inlet port is in fluid communication with the chamber. Suitably the surgical port comprises an outlet port. The outlet port may provide a fluid communication path from inside the port body, such as from inside the chamber, to an environment outside the surgical port. This can allow the inlet to communicate, via the outlet, with a surgical site. Fluid, such as gas, for example carbon dioxide, can be provided through the inlet so as to provide the fluid to the surgical site.

Suitably the surgical port comprises a first valve, such as a one-way valve, in communication with a first fluid path between the inlet port and the outlet port. This can restrict fluid flow to occur in one direction, such as from the inlet towards the outlet. Suitably the surgical port comprises a second valve, such as a one-way valve, located in a second fluid flow path between the first fluid path and the mechanism. This can restrict the fluid to flow along the first flow path. This can help prevent fluid leaking out of the surgical port along the second flow path.

Any one or more feature of any aspect above may be combined with any one or more feature of any other aspect above. These have not been written out in full here merely for the sake of brevity.

BRIEF DESCRIPTION OF THE DRAWINGS

The present invention will now be described by way of example only with reference to the accompanying drawings. In the drawings:

FIGS. 3a-3b show another locator coupled to a surgical port with the locator in relatively (a) contracted and (b) extended configurations;
FIGS. 4a-4b show another locator coupled to a surgical port with the locator in relatively (a) contracted and (b) extended configurations.

DETAILED DESCRIPTION

The port carriers or port locators illustrated in the figures allow control of the position and/or orientation of a surgical port so as to maintain a desired relationship between the surgical port and a robot arm (and therefore also between the surgical port and an instrument or tool shaft coupled to the robot arm).

In one example, the position of the surgical port can be controlled as the robot arm is moved towards the surgical port. For example, the tool shaft may be moved through the surgical port in an inward direction at a given desired rate of movement. The position of the surgical port can be controlled to move towards the robot arm at the same desired rate of movement so that the shaft can pass smoothly through the surgical port without disturbing its position.

In another example, the orientation of the surgical port can be controlled as the robot arm changes its orientation to more easily accommodate the shaft passing through the surgical port.

Figure 1:
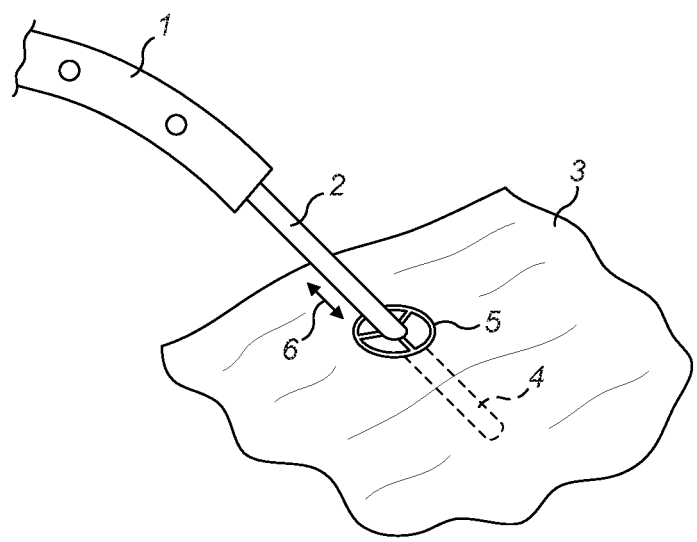
FIG. 1 shows a prior art surgical port.
Figure 2:
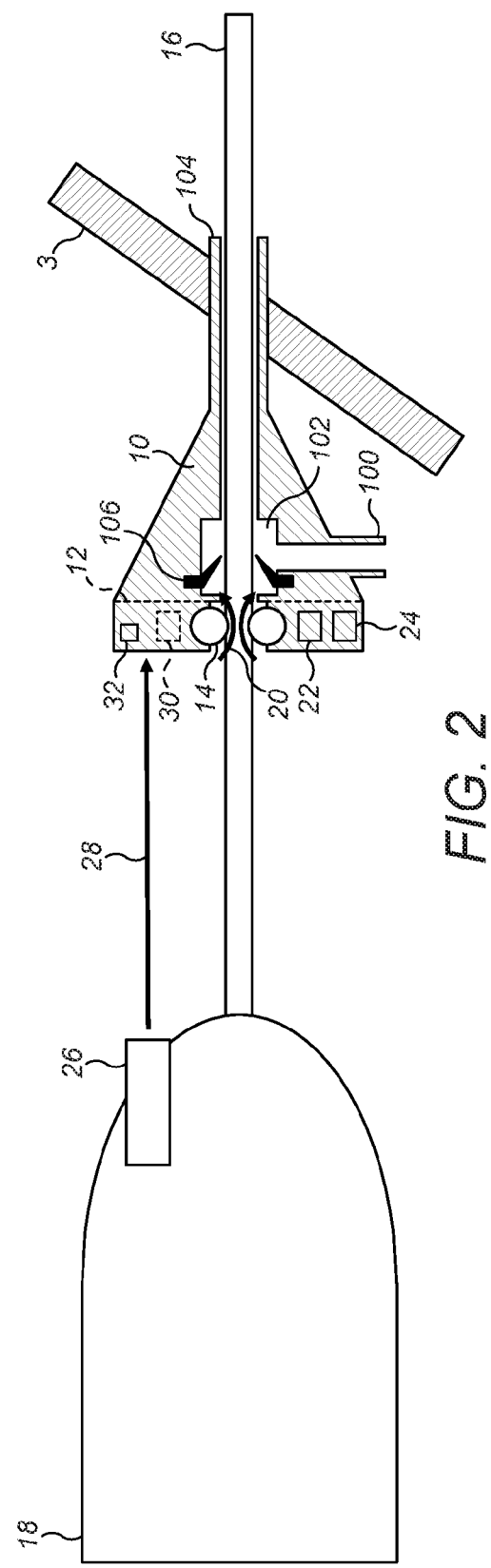
FIG. 2 shows a locator coupled to a surgical port.

Referring to FIG. 2, the port carrier or port locator is coupled to a surgical port 10. The locator is coupled to the port 10 by an interface 12. The locator comprises an engaging mechanism 14 for engaging with the tool shaft 16; a wireless communications module (shown schematically at 22) for allowing communication between the locator and a remote device such as a robotic surgical system controller; and a motor (shown schematically at 24) for driving the engaging mechanism 14.

In the example shown, the engaging mechanism comprises a pair of opposing rollers 14. The rollers 14 are resiliently deformable to enable a secure frictional grip of the instrument or tool shaft 16 of the robot arm 18 between the rollers. The rollers can be made of any suitable material. Advantageously, the rollers (or any other engagement mechanism) can comprise a frictional coating, to enhance the frictional grip. The rollers (or, again, any other engagement mechanism) can additionally or alternatively comprise surface undulations, such as protrusions, recesses and/or ridges, for increasing the ability of the rollers 14 to grip the shaft 16. This can prove useful in maintaining a good frictional grip throughout a surgical procedure, when the shaft 16 can become covered in fluids common at surgical sites, such as blood.

The rollers 14 are arranged for rotation about an axis extending out of the plane of FIG. 2, as indicated by the arrows 20. The engaging mechanism could comprise more than two rollers 14. For example, three rollers could be arranged in a triangular configuration, or four rollers could be arranged in a square configuration. Other numbers and/or configurations of rollers 14 are also possible.

In another example (not shown), the tool shaft comprises exterior ridges (with corresponding recesses between the ridges) or indentations, which are provided around at least a portion of the circumference of the shaft and extend along at least a portion of the length of the shaft. In some examples the rollers comprise protrusions spaced about the circumference of the rollers to engage with the recesses or the indentations on the shaft. This arrangement can form a rack and pinion type engaging mechanism. This arrangement can provide increased resistance to slipping and can provide increased control over the relative position of the locator and the shaft.

A distance sensor 26 is provided on a distal end of the robot arm 18. In the example illustrated in FIG. 2, the sensor 26 is a laser sensor, and is arranged to determine the distance between the distal end of the robot arm 18 and the locator (as indicated by arrow 28). A communication module remote from the locator (not shown) can transmit the detected distance or a movement command to the wireless communications module 22 of the locator (this can alternatively, or additionally for example for redundancy, be transmitted by a wired connection (not shown)). The rollers 14 are arranged to be driven by the motor 24 in response to the transmitted signal.

In another example the sensor 26 is provided on the locator (shown schematically in dashed lines at 30). Providing the sensor 26 on the locator can enable the locator to be autonomous. In other words the locator can control itself. A power source such as a battery 32 can also be provided on the locator. Alternatively or additionally a wired connection can provide power to the locator, for example to the motor 24.

FIGS. 3(*a*) and (*b*) show an alternative configuration of a port carrier or locator. The locator shown in FIG. 3 is attached to the distal end of a robot arm 18. The locator comprises an extensible member 34 which carries an interface 36 at its end remote from the robot arm 18. The extensible member can vary in length from the retracted or contracted configuration shown in FIG. 3(*a*) to the extended configuration shown in FIG. 3(*b*).

The port carrier has a motor 38 which can drive the extensible member to extend or contract so as to adopt a desired length. In other words, the driving of the extensible member 34 by the motor 38 can control the distance between the locator (and hence the port 40) and the distal end of the robot arm 18. In one example the motor 38 is operatively coupled to a spool 42 about which the extensible member is coiled and to which it is attached. Driving the spool allows the extensible member to be extended and retracted.

In another example, the spool 42 could be mounted to the port 40 instead of to the distal end of the robot arm 18. In one example, the motor 38 could also be provided on (or attached to) the port 40. The configuration shown in FIG. 3 (where the spool 42 and motor 38 are provided on the distal end of the robot arm 18) advantageously enables the port 40 to remain relatively light in weight. This can make it easier to control the movement of the port.

In one example, the extensible member 34 is a coiled metal tape. In other examples, other suitable materials can be used. The tape is configured with a cross-sectional shape that resists bowing of the tape away from the shaft 16. This enables positional accuracy to be maintained. For example, the tape may have a generally U-shaped cross-section. Rigidity of motion can be provided by the instrument. In at least some examples this enables the use of a flexible extensible member 34 yet provides rigidity of motion of the interface (and hence the surgical port). This can mean that the interface is controllable such that its position relative to the seat is always determinable.

In one example the spool is resiliently biased towards one of extension or retraction to assist with extending or contracting the extensible member. In some examples, the motor 38 is engageable to assist or counter the biasing force (in other words the motor can for example generate force that balances or exceeds the biasing force). In one example the spool is biased by a resilient member such as a spring. In one example, the spool is resiliently biased towards a contracted state to assist in drawing the port 40 towards the distal end of the robot arm 18. In this example, the motor 38 can be engaged to balance the biasing force when the location of the interface and hence the port 40 is desired to remain constant with respect to the distal end of the robot arm 18.

The single member is arranged to permit motion over the full extent of the linear relative motion of the seat and the interface.

Referring now to FIGS. 4 (*a*) and (*b*), in another example the extensible member is an inflatable bag 44 that carries the interface 36 at its end remote from the robot arm 18. The extensible member can vary in length from the retracted or contracted configuration shown in FIG. 4(*a*) to the extended configuration shown in FIG. 4(*b*).

The port carrier or locator in this example also has a driver 38 which can drive the extensible member to extend or contract so as to adopt a desired length. In other words, the driving of the extensible member 44 by the motor 38 can control the distance between the interface (and hence the port 40) and the distal end of the robot arm 18. In this example the driver 38 may be a pump for controlling fluid pressure within the extensible member 44. The pump 38 can control fluid pressure in the inflatable bag 44 by controlling fluid flow through at least one valve into and/or out of the inflatable bag 44.

For example, to inflate the bag (and move the port 40 further away from the distal end of the robot arm 18), the pump 38 can be controlled to pump fluid such as gas into the inflatable bag 44. The increase in pressure within the bag 44 can cause it to expand along a portion of the length of the shaft 16 away from the robot arm 18. To deflate the bag (and move the port 40 towards the distal end of the robot arm 18), the pump 38 can be controlled to pump fluid such as gas out from the inflatable bag 44. The fluid could be pumped back into a fluid store (not shown) or let out into the atmosphere adjacent the locator. This may be suitable where the fluid is a gas. Alternatively or additionally to pumping the fluid out of the bag 44, a valve (which in some examples is an outlet valve) can be operated to open a fluid communication channel to a volume with a lower pressure than that inside the bag 44. For instance, the bag 44 might inflate at an internal pressure above atmospheric pressure, and the valve might open to the atmosphere to vent the fluid so as to allow the bag to deflate. The pump 38 can be used to assist this, which might make it quicker, and to enable the bag 44 to adopt a more contracted configuration than might be possible with venting to atmosphere alone. For example the pump can reduce the pressure in the bag to below ambient or atmospheric pressure.

Conveniently, the instrument shaft 16 passes through the interior of the inflatable bag 44. In this example, the bag 44 is coupled to the interface 36 in a sealed manner to enclose a sealed volume within the bag 44. Rigidity of the extensible member 44 both in contracted and extended configurations can be provided by the instrument shaft 16.

The inflatable bag 44 (which in some examples could be an inflatable sheath) is in some examples at least part of a sterile drape that is used to at least partially cover at least a portion of a robotic surgical system. For example, the sterile drape might cover the robot arm 18, and the instrument or tool might extend through the drape. Providing the extensible member 44 as part of the drape can provide a more uniform and/or consistent sterile barrier.

The gas might be carbon dioxide, a source of which may be provided in the robot arm 18 for insufflation. Using this gas for inflating the inflatable bag 44 as well can reduce the complexity of fluid conduits needed within the robot arm 18. Any other suitable fluid could be used instead. In another example, air can be pumped into the inflatable bag 44 for example from the atmosphere adjacent a portion of the robot arm 18, or adjacent the bag 44.

Where a gas suitable for insufflation such as carbon dioxide is used to inflate the inflatable bag 44, the inflatable bag 44 can form a portion of a fluid flow path for insufflating a surgical site. Valves (not shown) can be provided to outlet the gas from the inside of the bag 44 through the port 40 and towards the surgical site. In such examples, it is convenient for the inflatable bag 44 to be arranged to inflate at pressures above those used for insufflation. In this way, insufflation of a surgical site can be achieved independently of the state of the extensible member 44.

Where the bag 44 is not inflated, the insufflation gas can simply be allowed to pass through the bag 44. The pressure of the gas will not be sufficient to cause the bag 44 to inflate. Where the bag 44 is inflated, a valve such as a bleed valve or regulator valve (not shown) can be used to restrict gas flow to both ensure a sufficient pressure inside the bag 44 for inflation of the bag 44 and to allow gas at an appropriate pressure to be used for insufflation.

In these examples it is convenient if at least one one-way valve is provided along the fluid flow path between the interior of the inflatable bag 44 and the outlet of the port 40 into the surgical site to make sure that no contaminants from the surgical site can travel upstream into the bag 44. Alternatively or additionally one or more one-way valve can be provided in a fluid flow path between the robot arm 18 and an inlet into the inflatable bag 44. The inflatable bag 44 may be disposable, for example along with or as part of the surgical drape.

Figure 8:
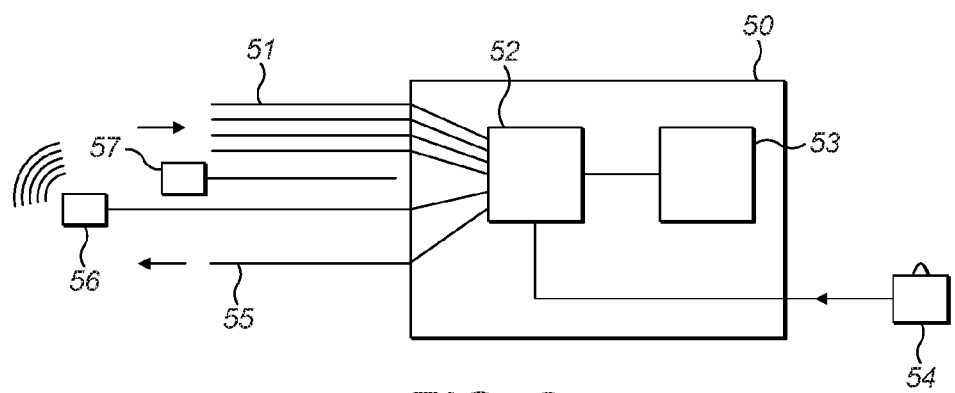
FIG. 8 illustrates a control device for the locator of any of FIGS. 2 to 7.

Referring to the various arrangements described, the driver (such as the motor or pump) is controlled by a motor controller 50 (see FIG. 8). As the robot arm moves, the motor controller computes the position and/or length required of the mechanism 14, 34, 44 in order to keep the port 10, 40 in place in an incision in the patient. In this way, the port can be kept in place without relying on it being attached to the incision and without it transmitting any significant force to the incision.

The port carrier shown in FIGS. 3 and 4 has a seat by means of which it is attached to the distal end of the robot arm 18. The seat could comprise a clamp which is tightened in position on the arm. The seat could mate to the robot arm by means of a snap fitting. The seat could be screwed on to the arm or attached to it by adhesive. Other methods of attachment are possible.

The seat is fixed to a part of the robot arm 18 that remains coaxial with a surgical instrument 16 during surgery. Thus it could be attached to the robot arm distally of the terminal joint of the robot arm, or distally of the most terminal joint of the robot arm whose axis is not coaxial with the instrument. In one example (not shown) there is a joint located distally of the attachment. The rotation axis of this joint is coaxial with the instrument 16.

The extensible member 34, 44 is attached rigidly to the seat. In the examples shown in the figures the extensible member has a linearly extending configuration which is convenient because it avoids the extensible member taking up excessive space.

The motor 38 can drive the motion of the extensible member in any suitable way. For example, a rotary motor may drive the spool 42 of the example shown in FIG. 3 directly, or via a belt. The motor may produce linear drive which can be transformed into rotary drive, for example by a rack and pinion type arrangement amongst others. There could be a pneumatic or hydraulic piston which acts analogously to the motor. There could be a single motor, piston or other device that provides the entire range of motion of the mechanism (e.g. the extensible mechanism). Alternatively the mechanism (e.g. the extensible mechanism) could have multiple drivers such as motors and/or pistons operating in series to provide the full range of motion.

Figure 5:
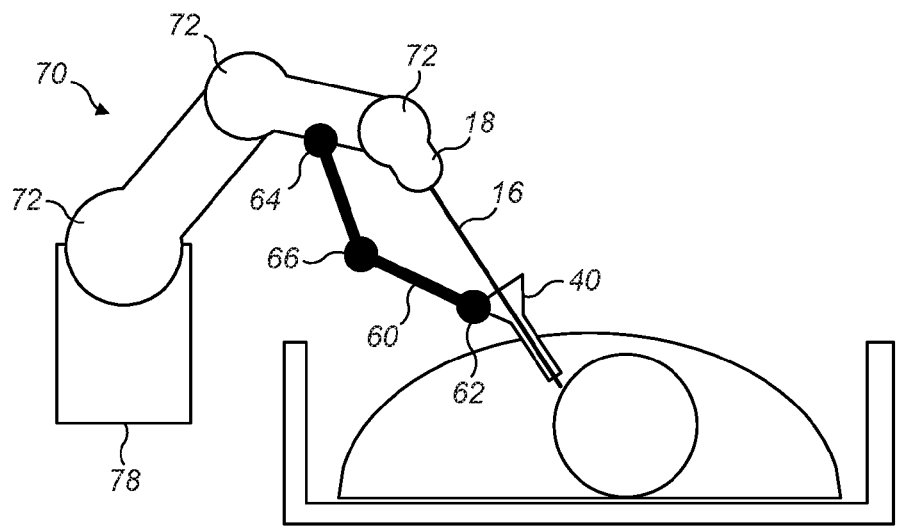
FIGS. 5 to 7 show other locators coupled to surgical ports.

Referring now to FIG. 5, in one example the locator comprises an articulated mechanism in the form of an articulated robot arm 60. An interface 62 couples one end of the articulated arm 60 to the port 40, and a seat 64 couples the other end of the articulated arm 60 to the robot arm (i.e. the main robot arm 70). The articulated arm 60 is articulated so as to enable linear relative motion between the interface 62 of the articulated arm and the distal end of the robot arm 18. The articulated arm comprises at least one articulated joint 66.

In the example shown in FIG. 5 the seat 64 of the articulated arm 60 is coupled to the main robot arm 70 proximally of the most distal joint 72, but distally of the next most distal joint 72. The articulated arm 60 in this example comprises one articulated joint 66. In general the number of articulations or articulated joints 66 needed in the articulated arm 60 depends on where the seat 64 is mounted to the main robot arm 70.

The articulated arm 60 has fewer articulations than the main robot arm 70. The articulated arm 60 can include one or more types of robotic joint such as revolute and prismatic joints. The configuration of joints can be chosen in dependence on the available volume that can be occupied by the articulated arm 60 and the volume it can sweep out during movement, and/or amongst other factors.

A driver (not shown) such as a motor, for example an electric motor, is operatively coupled to at least one of the at least one articulated joint 66 of the articulated arm 60. The motor is configured to apply a force between the seat 64 and the interface 62 to alter the configuration of the articulated arm 60. The at least one articulated joint 66 is in one example driven by the motor.

A piston such as a hydraulic or pneumatic piston or other device could be used to drive the articulated arm 60. There could be a single motor, piston or other device that provides the entire range of motion of the articulated arm 60. Alternatively the articulated arm 60 could have multiple devices operating in series to provide the full range of motion.

Figure 6:
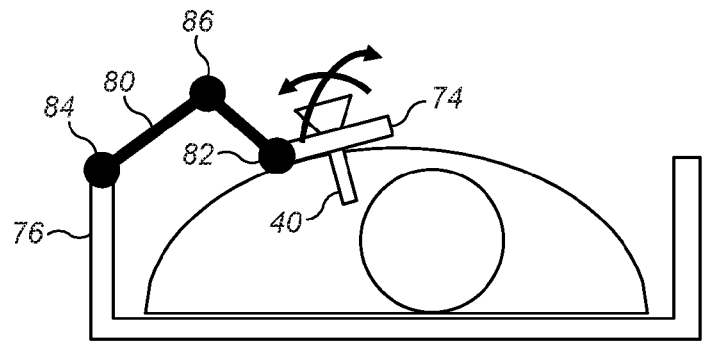

Further examples of locators will now be described with reference to FIGS. 6 and 7. FIG. 6 shows an articulated support mechanism 80 with a base 84 coupled to a patient support 76 such as a table and an interface 82 coupled to a gimbal system 74. In this example the articulated support 80 comprises one joint 86, but in other examples the support mechanism 80 can comprise a plurality of joints, at least one of which may be an articulated joint. The articulated support 80 can include one or more types of robotic joint such as revolute and prismatic joints. The port 40 is rotatably coupled to the gimbal system 74.

The support mechanism or support arm 80 comprises, in one example, a lock or locking mechanism (not shown) which enables at least one joint of the arm to be locked to restrict its movement. In this way the support arm 80 can be held firm when locked, then unlocked to enable manual or motorised movement of the arm, and then locked again when the arm is in the desired position. The locking of the arm enables it to remain firmly located during a surgical procedure, and can prevent accidental or inadvertent motion of the support arm 80.

The articulations of the support arm 80 can be driven in a manner analogous to the driving of the articulations of the articulated arm 60 as described above, but may be separately driven. The driving of the support arm 80 may enable the position of the port 40 to be changed between surgical procedures, and/or it may enable the position of the port 40 to be changed during a surgical procedure to match at least one of motion of the robot arm 18 and motion of a patient (such as motion caused by breathing). This control of the motion of the port 40 can reduce forces acting on the port 40 and hence forces transmitted to the incision in the patient.

Figure 7:
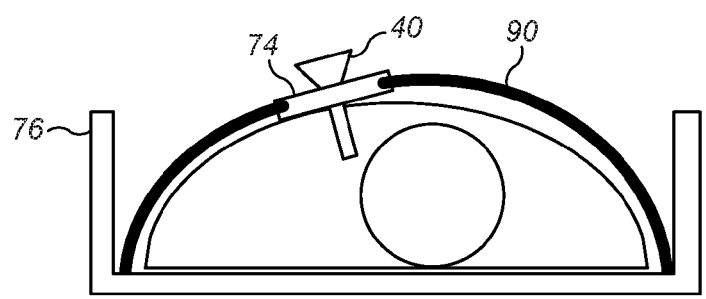

In the example shown in FIG. 7 the port 40 is held in place by a belt 90. In this example the belt is a solid belt. The solid belt can provide structural rigidity to the system. In other examples the belt may be more flexible. In such examples, structural rigidity can be provided at least partially by the tension in the belt holding the belt against an object such as a patient lying on the patient support 76. Referring again to FIG. 7, the belt 90 is provided in two portions, each of which are coupled to the patient support 76 at one end and to the gimbal system 74 at the other end.

The gimbal system 74 is driven to keep it (and hence the port 40) pointed in the desired direction. The gimbal system is in one example driven by a motor provided on the gimbal system itself. The gimbal system 74 can be in communication with a remote device such as a portion of the robotic surgical system through a wired connection or through a wireless connection or both. The gimbal system may therefore comprise a wired connection and/or a wireless communication module (not shown). The wired connection may alternatively or additionally be used to provide power to the gimbal system 74. A local power source such as a battery may be provided on the gimbal system 74.

The control of the gimbal system 74 and hence of the port 40 is in some examples independent of any instrument or the robot arm. This arrangement can be used to enable fully automatic instrument change: the robot arm can be employed in another action without worrying about the port location or orientation.

When moving an instrument shaft into and/or out of a surgical site, the distal portion of the robot arm (i.e. that portion of the robot arm to which the surgical instrument is attached) is typically constrained to move along one axis (an insertion/removal axis) to avoid exerting forces such as lateral forces on the surgical port. Suitably the support mechanism is arranged to permit motion of the interface in a direction perpendicular to the insertion/removal axis. In other words, the support mechanism can allow movement of the interface away from the axis along which the surgical instrument is constrained to move during insertion and removal.

Referring again to FIG. 2, in some examples the port for use with any of the locators described above comprises an inlet port 100. The inlet port 100 is in fluid communication with a chamber 102, which is in fluid communication with an outlet port 104. Gas such as carbon dioxide for insufflation can be provided to a surgical site via the inlet port 100, the chamber 102 and the outlet port 104.

In some examples the chamber 102 comprises another outlet, towards the distal end of the robot arm. A valve 106 is provided to restrict or prevent the flow of the fluid through this outlet. The valve can be a one-way valve. This can prevent any undesirable build-up of pressure behind the valve 106. In some examples a one-way valve can be provided along the flow path from the chamber 102 to the outlet 104. This can restrict or prevent fluid flow from a surgical cavity into the port.

Figure 9:
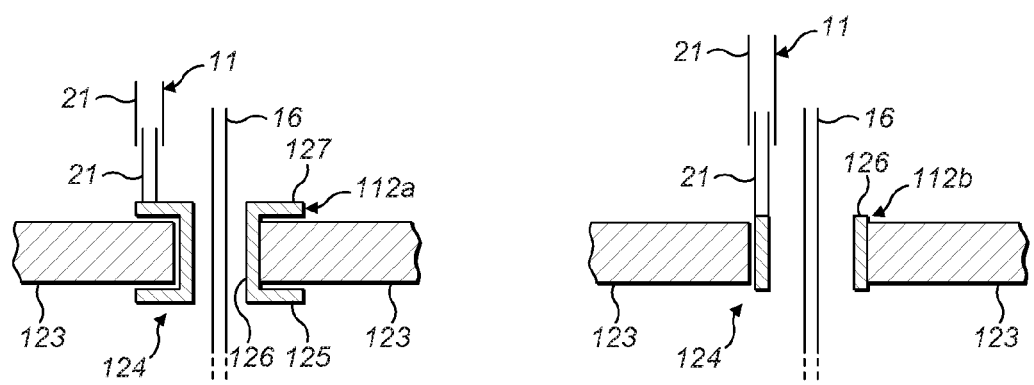
FIG. 9 illustrates surgical ports.

The ports illustrated in FIGS. 3 to 5 are attached rigidly to the distal end of the extensible member 34, 44 or articulated arm 60. The port can be a conventional surgical port, or it could be simplified due to the reduced need for the port to hold itself in place in the incision. FIG. 9 shows two examples of how the port can be configured. FIG. 9 shows cross-sections through the areas around incisions 124 in the skin 123 of a patient. In the left-hand part of FIG. 9 the port 112a has an annual inner wall 125 which sits on the inside of the patient's skin radially outward of the incision 124 and an annual outer wall 127 which sits on the outside of the patient's skin radially outward of the incision 124. The inner wall could be expanded into position once the port has been located in the incision. A central tube 126 runs through the patient's skin at the incision site and connects the inner and outer walls 125, 127. In the right-hand part of FIG. 9 the port 112b consists simply of a central tube 126 running through the patient's skin at the incision site. It does not extend radially outwards of the incision inside or outside the skin.

In another design the port could be as shown at the left-hand side of FIG. 9 but without the inner wall 125. This latter design is advantageous in that it can easily be inserted into the patient without the need to stretch the incision to accommodate the inner flange 125 or to have a complex port design in which the inner flange is expandable, but the outer flange 127 can still assist in resisting motion of the port. In each of these examples the port has a part that passes through the patient's skin at the incision site and can thereby maintain separation between the skin and the instrument 16. The instrument 16 is inserted through that part of the port.

The surgical instrument 16 extends from the distal end of the arm 18. The instrument could, for example, be a cutting, gripping or sensing instrument. The instrument extends linearly away from the arm 18. The instrument passes through the port 112. In this example the instrument 16 is not connected to the port 112 other than via its attachment to the arm 18. Since the instrument is free from the port in this way, lateral movement of the instrument, for example if its tip deflects when pressed on a hard object, will not be transmitted to the port unless the arm itself moves. This reduces the chance of the incision being damaged during an operation.

In some examples the port carrier does not provide linear travel to the instrument. It is not linked to the instrument distally of the distal end of the robot arm. It responds to movement of the arm and of the extensible member 34, 44 or articulated arm 60 but not to separate movement of the instrument.

The main robot arm 70 has a plurality of joints 72 along its length, which allow the position of the distal end of the arm to be moved relative to the base 78 of the arm. Each joint is equipped with a position encoder (not shown) which detects the configuration of the joint. The outputs of the position encoders are passed to the control unit 50 as indicated at 51 in FIG. 8. The motor may incorporate or be equipped with a position encoder that provides the control unit 50 with information indicating the current length of the extensible member 34, 44 and/or the current position of the articulated arm 60 or the current position of the locator on the shaft 16 (as appropriate). Alternatively, there may be one or more separate position encoders for the extensible member 34, 44, the articulated arm 60 and/or the locator mounted on the shaft 16.

The control unit 50 comprises a processor 52 and a memory 53. The memory 53 stores in a non-transitory form a program comprising a series of instructions for execution by the processor to perform in the manner described below. The program models the operation of the robot arm so that based on the outputs from the position encoders the control unit can estimate the spatial position of the distal end of the arm 18. When an operation is to be carried out, an operator puts the robot arm in an initial configuration and attaches the port to an incision in the patient with the locator in a suitable configuration to hold the port in the desired location, for example with the extensible member 34, 44 of a suitable length to run from the robot arm to the port. At this point the controller is receiving position information from the position encoders, so it can calculate the position of the distal end of the arm and knows the length of the extensible member 34, 44 (in other examples it will know the position of the distal end of the articulated arm 60, support arm 80 and/or the locator on the shaft 16).

The operator then operates a user interface control 54 to signal to the processor that the current configuration is a reference configuration. Subsequently, during the course of an operation the robot arm will be moved, and the distance between the distal end of the robot arm and the port will vary. That movement can be computed by the processor 52 using the program stored in the memory 53. The processor can thereby determine the configuration required of the locator, such as the length required of the extensible member 34, 44, in order for the port 112 to remain in place in the incision in the patient. As that configuration changes the processor 52 commands the motor via a line 55 in order to cause the locator to adopt a configuration such that the port remains in place in the incision.

As the robot arm 18 inserts the instrument into the patient the locator moves the port towards the robot arm 18 (by controlling the engaging mechanism 14, by contracting the extensible member 34, 44, and/or by controlling the articulated arm 60) under the control of the controller 50, keeping the port in the correct place. As the robot arm 18 retracts the instrument from the patient the locator moves the port away from the robot arm 18 (by controlling the engaging mechanism 14, by extending the extensible member 34, 44, and/or by controlling the articulated arm 60) and provides the reaction force to keep the port in place. The motion of the engaging mechanism, the extensible mechanism and/or the articulated mechanism is synchronised in time and in displacement with motion of the arm.

The processor could use additional information. For example, an operating theatre in which the robot is located could be equipped with a sensor 56 that senses motion of the patient. The sensor could sense motion of the patient remotely, using for instance ultrasound or optical signals. In this way, if the incision moves, for example as the patient breathes, this motion can be taken into account by the processor to cause the port to remain at the position of the incision for the time being.

Figure 10:
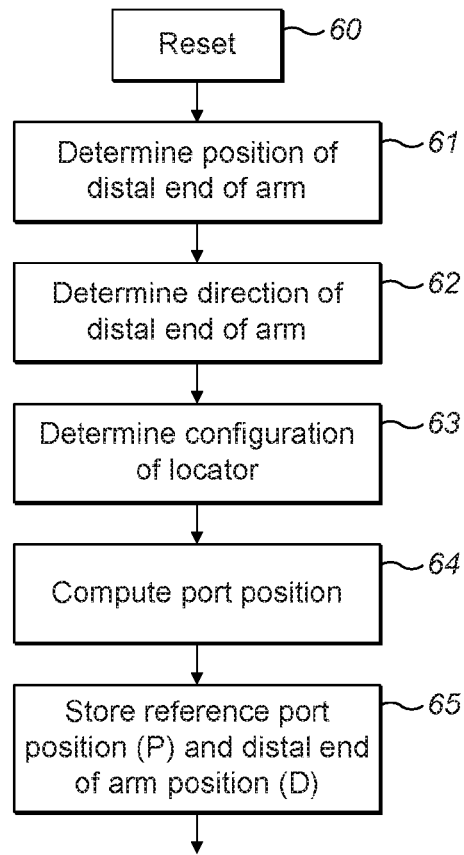
FIGS. 10 and 11 illustrate logic used by a controller.
Figure 11:
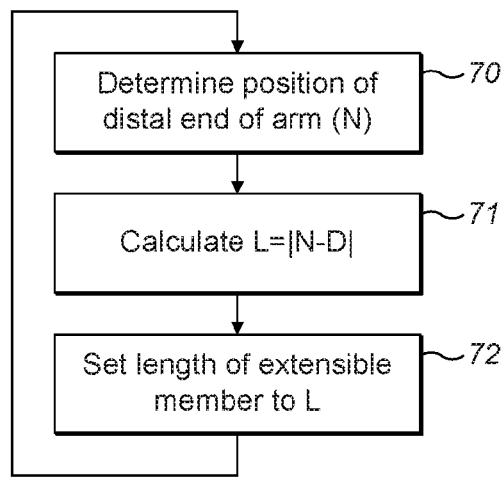

The logic implemented by the processor may be as illustrated in FIGS. 10 and 11.

FIG. 10 illustrates the actions following the resetting of the system in response to the control 43 being actuated (step 160). The initial position of the distal end of the robot arm ("D") is determined (step 161), as are the direction in which the distal end of the arm is pointing (step 162) and the configuration of the locator (step 163). This last step can include determining the length of the extensible member, determining the location of the locator on the shaft 16, determining the configuration of the articulated mechanism and/or determining the configuration of the support arm 80.

Then the position of the port ("P") can be computed as being the point offset by the determined separation in that direction from point D (step 164). For this step the controller can be pre-programmed with the relationship between the distal end of the arm and the direction of extension of the extensible member. The locations of P and optionally D are stored, for example as Cartesian coordinates (step 165).

FIG. 11 illustrates a control loop, with reference to FIGS. 3 and 4, when the robot is in operation. The new position ("N") of the distal end of the arm is determined (step 170). A desired length ("L") is determined as the magnitude of the offset between N and D (step 171). Then the motor is controlled to set the length of the extensible member to be L. This loop is repeated whilst the robot is in operation. The rate at which the loop is repeated will depend on the speed of motion of the robot, but it could, for example be repeated 20 times per second or faster. If the controller has knowledge of motion of the incision, this can be taken into account in step 171.

The port carrier could be equipped with one or more force sensors 57 that sense force on the port. There could be a single force sensor that senses force in the direction coaxial with the instrument. The output from this sensor could be used as an input to the processor in addition to or instead of the inputs discussed above. However, for this sensor to provide information on the stress on the port applied from the incision there needs to be a degree of adherence between the incision and the port, and in many situations it may be preferable for the port to be substantially freely floating in the incision in the direction parallel to the instrument axis.

In some examples, a surgical robot comprises a robot arm and a locator as defined above coupled to the robot arm. In some examples the surgical robot comprises a surgical tool or instrument coupled to the robot arm. A portion of the surgical tool is, in some examples, arranged to pass through the surgical port. In some examples, the surgical tool is substantially unsupported by the locator.

In some examples the surgical instrument comprises an instrument shaft and the locator is coupled to the robot arm by being coupled to the instrument shaft.

The motion of the engaging mechanism, the extensible mechanism, the articulated mechanism and/or the support mechanism under the control of the control unit 50 can resist any frictional force between instrument and port. This can help to avoid the port being dislodged from the incision when the instrument moves relative to the patient.

In some examples, the mechanism described above can be lighter and more compact than some prior designs of port retention mechanism since it does not have to support the instrument. This means it can take up less space, allowing ports to be placed closer together. This is especially significant for surgical procedures in confined spaces, for example ear nose and throat (ENT) surgery.

Since the port does not support the instrument in some examples, the port and the port carrier can be removed from the robot arm independently of the instrument. This means the system can perform surgical procedures with self-securing ports or that do not require ports without unnecessary encumbrance. Similarly, the instrument can be removed from the robot arm whilst the port remains in place.

In some examples, the extensible mechanism is driven for both elongation and contraction. The extensible mechanism could be biased to its extended or contracted configuration, for example by one or more elastic elements such as a spring. Then the extensible mechanism could be driven for motion in one direction, and motion in the other direction could be provided or at least assisted by the biasing means.

In some examples, the port carrier is attached to the robot arm near the distal end of the arm. Conveniently it can be located distally of the terminal joint of the arm, distally of the second most terminal joint of the arm or distally of the third most terminal joint of the arm. In one embodiment it can be attached to the arm between the most distal (terminal) joint of the arm and the second most distal joint of the arm. Conveniently any joints located distally of the attachment of the port carrier to the arm are such as to be incapable of varying the direction of the axis of the instrument relative to the port carrier. Such joints could permit linear motion of the instrument along its axis and/or rotation of the instrument about its axis. The axis of the instrument may be defined by the direction of elongation of the instrument. The axis of the instrument may be defined between (a) the port and (b) one of the location of attachment of the instrument to the arm and the location of attachment of the port carrier to the arm. The instrument is conveniently attached to the arm distally of the location of attachment of the port carrier to the arm. The port carrier could be located elsewhere on the arm. For example it could be located near the base of the arm.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A port locator of a surgical port of a surgical robot system, where the surgical robot system includes an instrument attached to a robot arm, the instrument having an instrument shaft configured to pass through the surgical port to a surgical site, the port locator comprising:
   an interface configured to couple to the surgical port;
   a mechanism coupled to the interface and configured to apply a force to the interface as the interface moves relative to the instrument shaft at the surgical site; and
   a controller including a processor configured to estimate the position of a part of the robot arm, the controller configured to control the mechanism in dependence on the estimated position of the part of the robot arm such that as the robot arm moves the instrument, the mechanism provides a force to keep the port in place at the surgical site.

2. A port locator as claimed in claim 1, further comprising a surgical port attached to the interface.

3. A surgical robot comprising: a robot arm and a port locator coupled to the robot arm;
   wherein the port locator includes:
     an interface configured to couple to a surgical port;
     a mechanism coupled to the interface and configured to apply a force to the interface as the interface moves relative to the instrument shaft at the surgical site; and
     a controller including a processor configured to estimate the position of a part of the robot arm, the controller configured to control the mechanism in dependence on the estimated position of the part of the robot arm such that as the robot arm moves the instrument, the mechanism provides a force to keep the port in place at the surgical site.

4. A surgical robot as claimed in claim 3 comprising the instrument attached to the robot arm, wherein a portion of the instrument is arranged to pass through the surgical port.

5. A surgical robot as claimed in claim 4, wherein the instrument is substantially unsupported by the port locator.

6. A surgical robot as claimed in claim 3 comprising the instrument with the instrument shaft, wherein the port locator is coupled to the robot arm by being coupled to the instrument shaft.

7. A port locator as claimed in claim 1, wherein:
   the port locator comprises a base configured to attach to a portion of a patient support;
   the mechanism is a support mechanism linking the base and the interface, the support mechanism permitting at least one of translational and rotational movement of the interface relative to the base; and
   the controller is configured to control at least one of the position and orientation of the interface relative to the base in dependence on the position of the robot arm.

8. A port locator as claimed in claim 7, wherein the support mechanism comprises a lock having:
   a locked configuration configured to at least partially restrict movement of the support mechanism, and
   an unlocked configuration configured to at least partially permit movement of the support mechanism.

9. A port locator as claimed in claim 7, wherein the support mechanism comprises at least one of an articulated support arm and a belt.

10. A port locator as claimed in claim 7, wherein the support mechanism comprises a rotational mechanism permitting rotation of the interface relative to the base.

11. A port locator as claimed in claim 7, wherein the support mechanism comprises a support mechanism driver configured to alter the configuration of the support mechanism by altering at least one of the translational configuration of the interface relative to the base and the rotational configuration of the interface relative to the base.

12. A port locator as claimed in claim 7, wherein the support mechanism is arranged to permit motion of the interface in a direction perpendicular to that of a direction of insertion or removal of the instrument shaft through the surgical port.

13. A port locator as claimed 1, further comprising a seat configured to attach to the robot arm;
   wherein the mechanism links the seat and the interface and permits linear relative motion of the seat and the interface;
   wherein the controller is configured to control the position of the seat relative to the interface in dependence on the position of the robot arm; and
   wherein the mechanism includes one of a single member permitting the linear relative motion and an articulated mechanism.

14. A port locator as claimed in claim 13, wherein the single member is an extensible member.

15. A port locator as claimed in claim 14, comprising an extensible member driver configured to alter the configuration of the extensible member.

16. A port locator as claimed in claim 13, wherein the articulated mechanism comprises a plurality of joints between the seat and the interface.

17. A port locator as claimed in claim 13, comprising an articulated mechanism driver configured to apply a force between the seat and the interface to alter the configuration of the articulated mechanism.

18. A port locator as claimed in claim 14, wherein the extensible member includes:
   an inlet port configured to allow fluid into an interior of the extensible member, and the extensible member is arranged to extend in response to the inlet of fluid into the interior; and
   an outlet fluid path configured to allow fluid to escape from the interior of the extensible member, the outlet fluid path being provided through at least one of the inlet port and an outlet port.

19. A port locator as claimed in claim 1, wherein:
   the mechanism is an engaging mechanism configured to engage with the instrument shaft of the robot arm to permit linear relative motion of the interface and the robot arm; and the controller is configured to control the position of the interface relative to the robot arm in dependence on the position of the robot arm.

20. A port locator as claimed in claim 19, wherein the engaging mechanism comprises a frictional coating configured to frictionally engage with the instrument shaft.

* * * * *